United States Patent [19]

Beuther et al.

[11] Patent Number: 5,779,965
[45] Date of Patent: Jul. 14, 1998

[54] DOUBLE NIP EMBOSSING

[75] Inventors: Paul Douglas Beuther, Neenah; Tammy Lynn Baum, Fremont, both of Wis.; Anthony Mark Gambaro, Conway, Ak.; David Robert Gruber, Neenah; Jeffrey Dean Lindsay, Appleton, both of Wis.

[73] Assignee: Kimberly-Clark Worldwide, Inc., Neenah, Wis.

[21] Appl. No.: 708,239

[22] Filed: Sep. 3, 1996

[51] Int. Cl.$^6$ .................................................. B29C 43/22
[52] U.S. Cl. .......................... 264/280; 264/282; 264/284; 264/293; 264/294; 264/296; 425/385; 425/394; 493/338; 493/467
[58] Field of Search .................................. 264/282, 284, 264/293, 296, 280, 294; 425/363, 385, 394; 493/338, 339, 467

[56] References Cited

U.S. PATENT DOCUMENTS

| | | | |
|---|---|---|---|
| 2,728,950 | 1/1956 | Annesser | 264/284 |
| 3,170,974 | 2/1965 | Jacobs | 264/284 |
| 3,611,919 | 10/1971 | Thomas | 101/23 |
| 4,144,008 | 3/1979 | Schwarz | 425/363 |
| 4,153,664 | 5/1979 | Sabee | 264/282 |
| 4,245,013 | 1/1981 | Clegg et al. | 429/144 |
| 4,387,144 | 6/1983 | McCallum et al. | 429/251 |
| 4,682,540 | 7/1987 | Eastman et al. | 101/32 |
| 4,859,519 | 8/1989 | Cabe, Jr. et al. | 428/131 |
| 5,069,548 | 12/1991 | Boehnlein | 356/376 |
| 5,087,191 | 2/1992 | Heise et al. | 425/335 |
| 5,562,805 | 10/1996 | Kamps et al. | 264/282 |

FOREIGN PATENT DOCUMENTS 0 631 014  12/1994  European Pat. Off. .
5-69482   3/1993  Japan .

OTHER PUBLICATIONS

Bieman, L. H.; Harding, K. G. and Boehnlein, A., "Absolute Measurement Using Field Shifted Moire", SPIE vol. 1614 (1991), pp. 259–264.

Harding, K. G., "Moire Techniques For Industrial Inspection", *Lasers & Applications*, Nov. 1983, pp. 73–78.

Harding, K. G. and Tait, R., "Moire Techniques Applied to Automated Inspection of Machined Parts" (Paper Submitted to SME Vision '86 Conference).

Bieman, L. H., "3–D Non–Contact Surface Analysis", Medar, Inc. Publication, pp. 1–4.

*Primary Examiner*—Jan H. Silbaugh
*Assistant Examiner*—Mark Eashoo
*Attorney, Agent, or Firm*—Gregory E. Croft

[57] ABSTRACT

The crispness or clarity of embossed tissue is improved by embossing the tissue twice in two successive embossing nips formed between a rigid engraved embossing roll and a resilient backing roll. The hardness of the resilient backing roll in the first embossing nip is less than the hardness of the resilient backing roll in the second embossing nip. This form of double nip embossing is particularly effective for embossing tissue webs having high bulk and resiliency, such as soft uncreped throughdried tissues, which cannot be satisfactorily embossed by conventional methods.

21 Claims, 11 Drawing Sheets

Exemplary embossing measurement using 11 sets of lines to define a butterfly shape (the representation). The mean depth of each of the eleven line segments is compared to the average depth of the surrounding pair of parallel lines outside the embossment, resulting in 11 height differences.

The median of these 11 values is the placement specific embossing depth for the selected click location (the pixel at which the mouse is clicked, corresponding to the lower end of line segment 1, the main body of the butterfly). The embossing clarity for the selected embossment is obtained by scanning a 3 x 3 pixel area around the clickpoint and recalculating the placement specific embossing depth using each of those 9 pixels as if it were the click point (moving all 33 line segments appropriately). The clickpoint providing the maximum embossing depth (median of the 11 sets of depth comparisons) is used as the reference click point to provide the embossing depth for the selected embossment. The selected line embossment has an embossing depth of 0.157 mm.
Two profile selections are also shown.

FIG. 5A

| | Image file: | 15_f2ds2.img | | | Embossing sample 13 (double nip) | | | | | | | | | | |
|---|---|---|---|---|---|---|---|---|---|---|---|---|---|---|---|
| | Line #: | 1 | 2 | 3 | 4 | 5 | 6 | 7 | 8 | 9 | 10 | 11 | | | |
| | I1 | 348 | 415 | 433 | 380 | 400 | 363 | 333 | 408 | 325 | 315 | 297 | | | |
| | J1 | 234 | 188 | 218 | 189 | 240 | 255 | 202 | 319 | 145 | 260 | 234 | | | |
| | I2 | 397 | 442 | 485 | 383 | 432 | 364 | 318 | 443 | 353 | 306 | 275 | | | |
| | J2 | 212 | 149 | 237 | 140 | 271 | 291 | 178 | 299 | 116 | 290 | 214 | | | |
| | EmbAvg | -0.317 | 0.031 | -0.262 | -0.205 | -0.428 | -0.472 | -0.238 | -0.448 | -0.52 | -0.217 | -0.343 | | | |
| | Ext1 | -0.188 | 0.203 | 0.078 | -0.007 | -0.358 | -0.321 | -0.118 | -0.187 | -0.277 | -0.095 | -0.272 | I1, J1 | 347 | Mean | 233 |
| | Ext2 | -0.207 | 0.188 | 0.04 | -0.207 | -0.123 | -0.28 | -0.176 | -0.325 | -0.361 | -0.227 | -0.296 | Median | 0.151 | St.dev. |
| | Mn.Diff | 0.12 | 0.165 | 0.321 | 0.097 | 0.188 | 0.171 | 0.091 | 0.192 | 0.201 | 0.056 | 0.059 | 0.165 | | 0.0775 |
| | | | | | | | | | | | | | | | | |
| | EmbAvg | -0.314 | 0.036 | -0.261 | -0.206 | -0.418 | -0.466 | -0.238 | -0.443 | -0.52 | -0.202 | -0.335 | | | | |
| | Ext1 | -0.183 | 0.204 | 0.078 | 0.002 | -0.354 | -0.319 | -0.129 | -0.172 | -0.274 | -0.095 | -0.275 | I1, J1 | 348 | Mean | 233 |
| | Ext2 | -0.206 | 0.188 | 0.044 | -0.206 | -0.107 | -0.3 | -0.169 | -0.322 | -0.382 | -0.23 | -0.288 | Median | 0.1472 | St.dev. |
| | Mn.Diff | 0.119 | 0.16 | 0.322 | 0.104 | 0.188 | 0.156 | 0.089 | 0.196 | 0.192 | 0.04 | 0.053 | 0.156 | | 0.0795 |
| | | | | | | | | | | | | | | | | |
| | EmbAvg | -0.311 | 0.04 | -0.261 | -0.21 | -0.409 | -0.452 | -0.243 | -0.439 | -0.517 | -0.182 | -0.328 | | | | |
| | Ext1 | -0.178 | 0.205 | 0.079 | 0.012 | -0.351 | -0.318 | -0.142 | -0.157 | -0.272 | -0.099 | -0.28 | I1, J1 | 349 | Mean | 233 |
| | Ext2 | -0.204 | 0.188 | 0.047 | -0.206 | -0.092 | -0.331 | -0.159 | -0.319 | -0.403 | -0.239 | -0.282 | Median | 0.1418 | St.dev. |
| | Mn.Diff | 0.12 | 0.157 | 0.323 | 0.113 | 0.188 | 0.127 | 0.092 | 0.201 | 0.179 | 0.013 | 0.047 | 0.127 | | 0.0835 |
| | | | | | | | | | | | | | | | | |
| | EmbAvg | -0.324 | 0.03 | -0.263 | -0.202 | -0.431 | -0.466 | -0.25 | -0.452 | -0.519 | -0.212 | -0.352 | | | | |
| | Ext1 | -0.186 | 0.205 | 0.074 | -0.005 | -0.352 | -0.317 | -0.126 | -0.17 | -0.274 | -0.092 | -0.267 | I1, J1 | 347 | Mean | 234 |
| | Ext2 | -0.221 | 0.184 | 0.024 | -0.203 | -0.138 | -0.272 | -0.18 | -0.326 | -0.381 | -0.226 | -0.296 | Median | 0.1515 | St.dev. |
| | Mn.Diff | 0.12 | 0.164 | 0.312 | 0.098 | 0.185 | 0.171 | 0.097 | 0.204 | 0.192 | 0.053 | 0.071 | 0.164 | | 0.074 |

| # | Label | | | | | | | | | | | | | | | | |
|---|---|---|---|---|---|---|---|---|---|---|---|---|---|---|---|---|---|
| 27 | EmbAvg | -0.321 | 0.036 | -0.263 | -0.204 | -0.421 | -0.462 | -0.247 | -0.448 | -0.516 | -0.195 | -0.346 | | | | | |
| 28 | Ext1 | -0.183 | 0.204 | 0.075 | 0.004 | -0.349 | -0.315 | -0.134 | -0.157 | -0.27 | -0.093 | -0.271 | I1, J1 | 348 | 234 | | |
| 29 | Ext2 | -0.22 | 0.183 | 0.029 | -0.202 | -0.121 | -0.291 | -0.173 | -0.322 | -0.403 | -0.229 | -0.286 | Median | Mean | St.dev. | | |
| 30 | Mn.Diff | 0.119 | 0.157 | 0.315 | 0.106 | 0.186 | 0.159 | 0.094 | 0.209 | 0.179 | 0.034 | 0.067 | 0.157 | 0.1477 | 0.077 | | |
| 31 | | | | | | | | | | | | | | | | | |
| 32 | EmbAvg | -0.319 | 0.04 | -0.262 | -0.208 | -0.411 | -0.448 | -0.249 | -0.446 | -0.503 | -0.173 | -0.338 | | | | | |
| 33 | Ext1 | -0.18 | 0.206 | 0.075 | 0.015 | -0.345 | -0.314 | -0.146 | -0.145 | -0.267 | -0.097 | -0.274 | I1, J1 | 349 | 234 | | |
| 34 | Ext2 | -0.219 | 0.183 | 0.033 | -0.202 | -0.105 | -0.321 | -0.164 | -0.318 | -0.428 | -0.24 | -0.278 | Median | Mean | St.dev. | | |
| 35 | Mn.Diff | 0.12 | 0.155 | 0.316 | 0.115 | 0.186 | 0.13 | 0.094 | 0.214 | 0.155 | 0.005 | 0.062 | 0.13 | 0.1411 | 0.0816 | | |
| 36 | | | | | | | | | | | | | | | | | |
| 37 | EmbAvg | -0.332 | 0.031 | -0.251 | -0.199 | -0.432 | -0.46 | -0.264 | -0.455 | -0.516 | -0.207 | -0.359 | | | | | |
| 38 | Ext1 | -0.188 | 0.205 | 0.066 | -0.003 | -0.344 | -0.314 | -0.133 | -0.158 | -0.271 | -0.089 | -0.26 | I1, J1 | 347 | 235 | | |
| 39 | Ext2 | -0.236 | 0.18 | 0.003 | -0.199 | -0.155 | -0.262 | -0.184 | -0.327 | -0.402 | -0.225 | -0.295 | Median | Mean | St.dev. | | |
| 40 | Mn.Diff | 0.12 | 0.161 | 0.285 | 0.097 | 0.183 | 0.172 | 0.106 | 0.212 | 0.179 | 0.049 | 0.082 | 0.161 | 0.1496 | 0.0671 | | |
| 41 | | | | | | | | | | | | | | | | | |
| 42 | EmbAvg | -0.33 | 0.036 | -0.26 | -0.202 | -0.423 | -0.457 | -0.259 | -0.453 | -0.503 | -0.188 | -0.356 | | | | | |
| 43 | Ext1 | -0.187 | 0.206 | 0.067 | 0.007 | -0.343 | -0.31 | -0.14 | -0.146 | -0.266 | -0.091 | -0.266 | I1, J1 | 348 | 235 | | |
| 44 | Ext2 | -0.235 | 0.179 | 0.01 | -0.197 | -0.136 | -0.281 | -0.179 | -0.323 | -0.428 | -0.229 | -0.285 | Median | Mean | St.dev. | | |
| 45 | Mn.Diff | 0.118 | 0.156 | 0.299 | 0.107 | 0.184 | 0.161 | 0.1 | 0.218 | 0.156 | 0.028 | 0.081 | 0.156 | 0.1462 | 0.0728 | | |
| 46 | | | | | | | | | | | | | | | | | |
| 47 | EmbAvg | -0.328 | 0.041 | -0.262 | -0.206 | -0.414 | -0.444 | -0.258 | -0.452 | -0.472 | -0.166 | -0.35 | | | | | |
| 48 | Ext1 | -0.187 | 0.207 | 0.068 | 0.018 | -0.34 | -0.309 | -0.15 | -0.135 | -0.267 | -0.095 | -0.27 | I1, J1 | 349 | 235 | | |
| 49 | Ext2 | -0.235 | 0.177 | 0.015 | -0.197 | -0.118 | -0.31 | -0.17 | -0.319 | -0.459 | -0.241 | -0.275 | Median | Mean | St.dev. | | |
| 50 | Mn.Diff | 0.117 | 0.151 | 0.303 | 0.117 | 0.185 | 0.135 | 0.097 | 0.224 | 0.109 | -0.002 | 0.078 | 0.117 | 0.1376 | 0.0798 | | |
| 51 | | | | | | | | | | | | | MaxMed | MedMax | MaxMn | MnMax | i1 click | j1 click |
| 52 | Col.Max: | 0.12 | 0.165 | 0.323 | 0.117 | 0.188 | 0.172 | 0.106 | 0.224 | 0.201 | 0.056 | 0.082 | 0.165 | 0.165 | 0.152 | 0.159 | 348 | 234 |

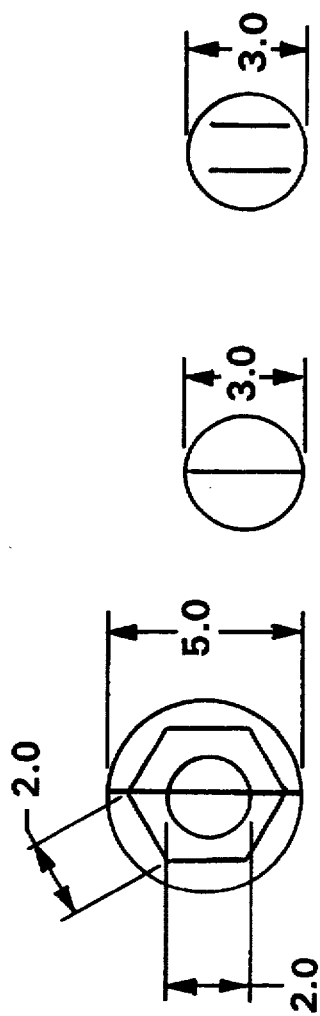
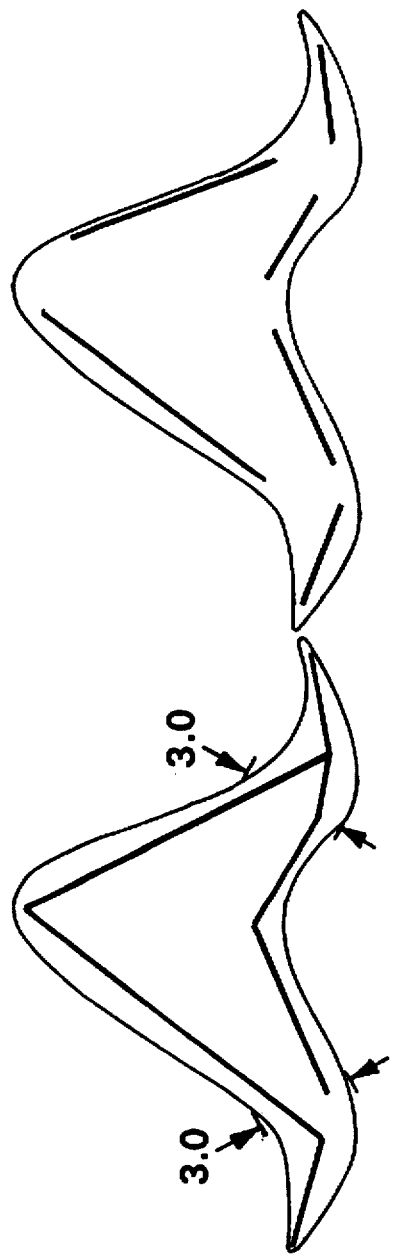

DOUBLE NIP EMBOSSING

This is a nonprovisional application having the benefit of copending provisional application Ser. No. 60/011,927 filed Feb. 20, 1996.

BACKGROUND OF THE INVENTION

Embossing is a well known means for imparting bulk and aesthetics to cellulosic sheets useful as paper towels, bath tissue, facial tissue and the like. There are a wide variety of embossing methods that can be used for this purpose. However, the effectiveness of the chosen embossing method is greatly affected by the properties of the sheet being embossed. In particular, sheets that are relatively stiff tend to accept and hold an embossing pattern rather easily. Good examples of such sheets are those used for making creped kitchen towels. On the other hand, tissue sheets that are very soft and have low stiffness, such as those used for premium bath tissue, are more difficult to provide with a crisp embossing pattern. This is largely due to the nature of soft, flexible tissue sheets, which readily deform during embossing to accept the embossing elements, and thereafter significantly return toward their former state. This problem is more acute with the recently developed soft uncreped throughdried tissues as described in published European Patent Application No. 0631014 entitled "Soft Tissue", assigned to Kimberly-Clark Corporation, because these sheets are also very resilient in addition to being soft, high in bulk and having low stiffness. These properties are achieved in part through a process that avoids compressive operations in the drying of the tissue. Heretofore it has not been possible to impart to these sheets crisp embossing patterns that are retained for relatively long periods of time.

SUMMARY OF THE INVENTION

It has now been discovered that crisp embossing patterns can be imparted to soft uncreped throughdried webs by utilizing a double nip embossing method. The embossing pattern is initially formed in the first embossing nip using a rigid engraved embossing roll (such as an engraved steel embossing roll) and a resilient backing roll. The embossing pattern is "set" in the web by repeating the embossing process while using a second resilient backing roll that has a greater hardness than that of the first resilient backing roll. The visual crispness of the resulting embossing pattern is substantially greater than can be attained using only a single step embossing method, particularly after the tissue web has "aged" for a day or two, such as at standard TAPPI temperature and humidity conditions.

Hence in one aspect the invention resides in a method of embossing a cellulosic web comprising: (a) embossing the web in a first embossing nip formed between a rotating rigid embossing roll having a pattern of protruding embossing elements and a first rotating resilient backing roll to produce an embossed web having a pattern of embossments corresponding to the embossing element pattern and (b) thereafter embossing the web in a second embossing nip formed between a second rotating resilient backing roll and a rotating rigid embossing roll having a pattern of protruding embossing elements which is in registration with the pattern of embossments in the embossed web, wherein the Shore A hardness of the second resilient backing roll is greater than the Shore A hardness of the first resilient backing roll. In carrying out this method, the second embossing nip can utilize the same rigid (engraved) embossing roll used for the first nip or a second, independent, rigid embossing roll can be used. In either case, the embossing elements in the second embossing nip must be in registration with the embossments in the embossed web from the first embossing nip. If not, partially overlapping embossing patterns will be imparted to the web, which will not provide the desired crisp pattern.

More specifically, the invention resides in a method of embossing a soft, uncreped throughdried tissue web comprising: (a) embossing the web in a first embossing nip formed between a first rotating resilient backing roll and a rotating rigid embossing roll having a pattern of protruding embossing elements; and (b) embossing the embossed web, while supported on the surface of the rigid embossing roll, in a second embossing nip formed between the rigid embossing roll and a second rotating resilient backing roll, wherein the Shore A hardness of the second resilient backing roll is greater than the Shore A hardness of the first resilient backing roll.

In another aspect, the invention resides in a soft, embossed uncreped throughdried tissue web having an MD Stiffness Factor (hereinafter defined) of about 150 or less and a Mean Embossing Clarity (hereinafter defined) of about 0.10 millimeter or greater.

In a further aspect, the invention resides in a product made by any of the methods described herein.

The hardness of the resilient backing rolls can be characterized by the Shore A hardness, a well-known value measuring the penetratability of a given material. Shore A hardness is designated in terms of hardness points, sometimes referred to as "Durometer". The Shore A hardness of the second resilient backing roll is greater than that of the first resilient backing roll. More specifically, the difference in Shore A hardness between the second resilient backing roll and the first resilient backing roll can be about 5 Shore A hardness points or greater, more specifically from about 5 to about 70 Shore A hardness points or greater, still more specifically from about 10 to about 55 Shore A hardness points or greater, and still more specifically from about 25 to about 40 Shore A hardness points or greater. In terms of absolute values, the Shore A hardness of the first resilient backing roll can be from about 30 to about 95 Shore A hardness points, more specifically from about 40 to about 85 Shore A hardness points, and still more specifically from about 65 to about 75 Shore A hardness points. The Shore A hardness of the second resilient backing roll can be about 70 Shore A hardness points or greater, more specifically from about 80 to about 100 Shore A hardness points or greater, and still more specifically from about 90 to about 100 Shore A hardness points or greater.

The average static nip pressure applied to the web in the embossing nips is higher in the second nip, but is dependent upon the roll diameter, roll cover thickness and roll cover material. By way of illustration, static nip pressures were determined for embossing nips formed between an engraved steel roll and each of two different resilient rolls having nominal roll diameters of 230 millimeters, a cover thickness of 19 millimeters and a cover material of nitrile rubber. The two resilient rolls had a Shore A hardness of 70 and 97 Durometer, respectively. The average static nip pressure applied to the web while using the 70 Durometer roll was between 700 and 1000 kilopascals. For the 97 Durometer roll, the average static nip pressure was between 5000 and 7000 kilopascals. These two average static nip pressure ranges are suitable for the first and second embossing nips, respectively.

Although the method of this invention can be used to emboss any kind of web or sheet, it is particularly effective for soft uncreped throughdried tissue webs or tissue webs that have been noncompressibly dried to about 40 weight percent moisture or less. These webs can be characterized by a low MD Stiffness Factor, which can be about 150 or less, preferably about 100 or less, and suitably from about 50 to about 100. The MD Stiffness Factor is calculated by multiplying the MD Max Slope (hereinafter defined) by the square root of the quotient of the Caliper (hereinafter defined) divided by the number of plies. The units of the MD Stiffness Factor are (kilograms force per 3 inches)(microns)$^{0.5}$, but for simplicity the values of the MD Stiffness Factor are hereinafter referred to without units.

As used herein, "Caliper" is the thickness of a single sheet, but measured as the thickness of a stack of ten sheets and dividing the ten sheet thickness by ten, where each sheet within the stack is placed with the same side up. Caliper is expressed in microns. It is measured in accordance with TAPPI test methods T402 "Standard Conditioning and Testing Atmosphere For Paper, Board, Pulp Handsheets and Related Products" and T411 om-89 "Thickness (caliper) of Paper, Paperboard, and Combined Board" with Note 3 for stacked sheets. The micrometer used for carrying out T411 om-89 is a Bulk Micrometer (TMI Model 49-72-00, Amityville, N.Y.) having an anvil diameter of 4 1/16 inches (103.2 millimeters) and an anvil pressure of 220 grams of force per square inch (3.39 kilopascals).

The MD Max Slope is the maximum slope of the machine direction load/elongation curve for the tissue and by itself represents an alternative measure of softness. The units for the MD Max Slope are kilograms force per 3 inches (7.62 centimeters). The MD Max Slope of the uncreped throughdried tissues embossed in accordance with this invention can be about 10 or less, preferably about 5 or less, and suitably from about 3 to about 6.

The crispness of the resulting embossments can be objectively quantified by the Mean Embossing Clarity, which will be defined in detail in connection with the Drawings. In general, the method of determining the Mean Embossing Clarity involves an optical measurement technique based on moire interferometry that measures the surface topography of the embossed tissue and compares the depth of the topographical features of the embossed regions relative to the unembossed regions. The Mean Embossing Clarity for embossed tissues of this invention, expressed in millimeters, can be about 0.10 or greater, more specifically about 0.15 or greater, still more specifically from about 0.10 to about 0.20, and still more specifically from about 0.12 to about 0.18.

BRIEF DESCRIPTION OF THE DRAWINGS

FIGS. 5 and 5A show a larger display of the height map of FIG. 4, illustrating how to calculate embossing depths.

FIGS. 6A and 6B constitute a table displaying typical output data for the height map of FIG. 5.

FIGS. 8A, 8B and 8C illustrate the selection of representative profile lines for circular embossed regions.

FIGS. 9A and 9B illustrate the selection of representative profile lines for thick and thin embossed regions.

DETAILED DESCRIPTION OF THE DRAWINGS

Figure 1:
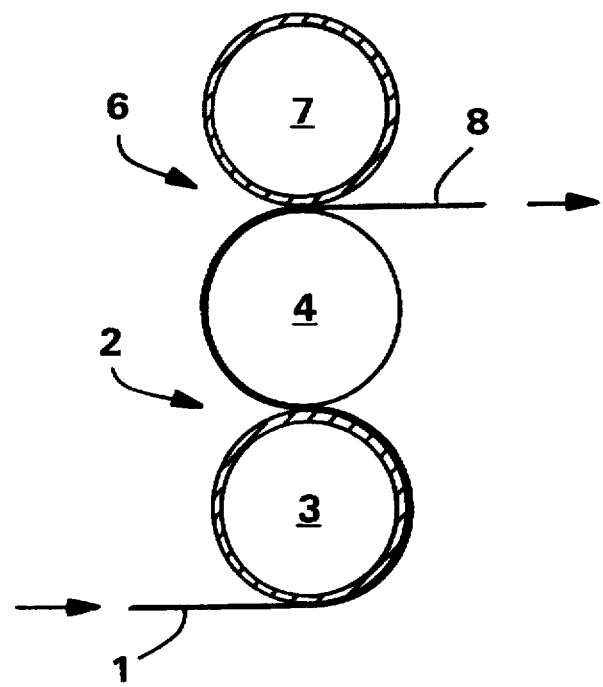
FIG. 1 is schematic illustration of a double nip embossing method in accordance with this invention, illustrating the use of a single rigid roll in between two resilient rolls.

Referring to FIG. 1, the invention will be described in greater detail. Shown is a tissue web 1, such as an uncreped throughdried tissue web, which is drawn through a first embossing nip 2 formed between a first resilient backing roll 3 and a rigid embossing roll 4. The surface of the rigid embossing roll contains a pattern of protrusions (embossing elements) which define the embossing pattern to be imparted to the web. Upon leaving the first embossing nip, the web possesses a pattern of embossments that corresponds to the embossing element pattern of the rigid embossing roll. The web is then carried to the second embossing nip 6 formed between the rigid embossing roll and a second resilient backing roll 7. In this embodiment, because the web is continuously supported by the same rigid embossing roll in both embossing nips, the embossments imparted to the web in the first embossing nip are necessarily in registration with the embossing elements of the rigid embossing roll of the second embossing nip. As discussed above, the hardness of the first resilient backing roll is less than that of the second resilient backing roll. This method provides for creating the embossing pattern in the first nip and setting the pattern in the second nip. The resulting twice-embossed web 8 has an embossing pattern with improved pattern definition or embossing clarity.

Figure 2:
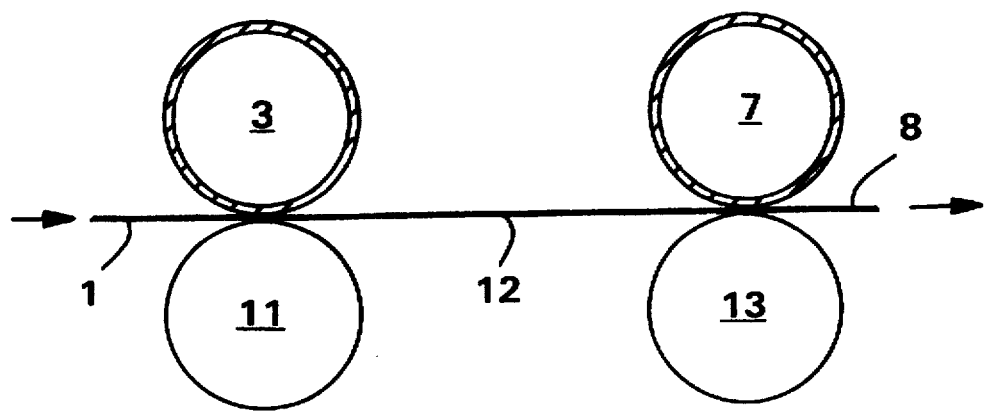
FIG. 2 is a schematic illustration of a double nip embossing method in accordance with this invention, illustrating the use of two consecutive independent embossing nips.

FIG. 2 illustrates an alternative means for carrying out the method of this invention using two consecutive independent embossing nips. Shown is the web 1 being directed into an embossing nip formed between a first rigid embossing roll 11 and a first resilient backing roll 3. The embossed web 12 leaving the first embossing nip is then passed through a second embossing nip formed between a second rigid embossing roll 13 and a second resilient backing roll 7. In this embodiment, care must be exercised to maintain the embossing elements of the second rigid embossing roll in registration with the embossments of the web leaving the first embossing nip. By this is meant that the embossing elements must contact the embossed web substantially within, preferably entirely within, the embossments of the web. Preferably the embossing pattern of the second rigid embossing roll is identical to the embossing pattern of the first rigid embossing roll. But it is within the scope of this invention that the second embossing pattern be different, provided that the embossing elements of the second rigid embossing roll fall within the embossments of the embossed web 12.

Measurement of Embossing Structure

Figure 3:
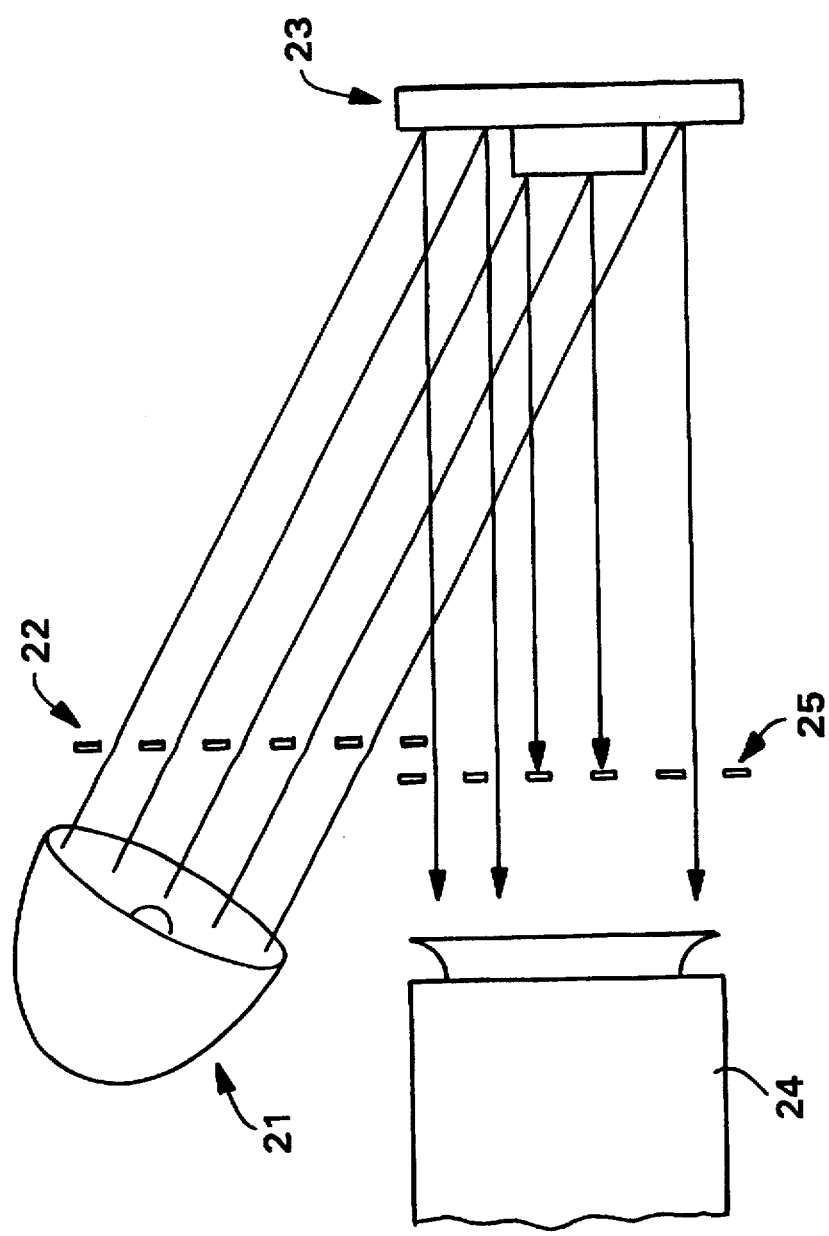
FIG. 3 is a schematic representation of the moire interferometry technique used to measure the Mean Embossing Depth of an embossed tissue sample.

The principle used to quantitatively measure the surface structure of embossed tissue is moire interferometry, which employs a sophisticated form of structured lighting as shown in FIG. 3. FIG. 3 shows several aspects of the basic method (simplified for clarity) for generating moire fringes that are related to the surface topography of an object. A light source 21 and a system of lenses and other hardware are used to shine light through a fine grid 22 of parallel black lines on glass (or a linear diffraction grating). The grid is projected (in focus) onto the sample 23 to be measured, resulting in a finely spaced series of light and dark stripes on the sample (only an edge view of the projected stripes is shown in FIG. 3). A video camera 24 (such as a CCD camera) views the sample through a similar grating or grid 25, allowing the striped pattern on the sample to interfere with the second grating to create interference fringes that are viewed by the camera, resulting in the well known moire effect. Depending on the surface height of each region of the object being measured, the CCD camera will see light or dark fringes created by interference between two sets of gratings. In FIG. 3, the elevated projection on the sample will coincide with a dark fringe because light stripes projected onto that elevated region destructively interfere with the grating over the camera to block out the light. Obviously, there are multiple heights that could cause a dark fringe to occur, so a single, static moire fringe pattern alone is inadequate to calculate the absolute height of each point on the surface (refinements such as field shifting that enable such a calculation are discussed below). When viewed with equipment similar to that shown in FIG. 3, the topographical structure of a surface will result in interference fringes with properties similar to bands on a contour plot. Closely spaced, narrow fringes may be due to steep gradients, while the fringes in flatter areas are few and broad. A video processor sends captured fringe images to a computer for processing, as described below, where the task of interpreting the fringe patterns is executed.

When properly implemented, moire interferometry can be used to accurately calculate the detailed surface structure of sample, providing data which can then be used to quantitatively assess the success of an embossing operation.

Experimental Equipment

Mean Embossing Clarity, as defined below, is a measure of embossing depth and is measured using a computer-controlled white-light field-shifted moire interferometer with a 38 millimeters field of view. The principles of a useful implementation of such a system are described in Bieman et al. (L. Bieman, K. Harding, and A. Boehnlein, "Absolute Measurement Using Field-Shifted Moire," SPIE Optical Conference Proceedings, Vol. 1614, pp. 259–264, 1991). A suitable commercial instrument for moire interferometry is the CADEYES® interferometer produced by Medar, Inc. (Farmington Hills, Mich.), constructed for a 38-mm field-of-view (a field of view within the range of 37 to 39.5 millimeters is adequate). The CADEYES® system uses optics similar to those shown in FIG. 3 with a white light source and additional lensing and a stepper motor to adjust the optical configuration for field shifting (a technique described below). A video processor sends captured fringe images to a PC computer for processing, allowing details of surface height to be back-calculated from the fringe patterns viewed by the video camera.

In the CADEYES moire interferometry system, each pixel in the CCD video image is said to belong to a moire fringe that is associated with a particular height range. The method of field-shifting, as described by Bieman et al. and in U.S. Pat. No. 5,069,548 to Boehnlein, herein incorporated by reference, is used to identify the fringe number for each point in the video image (indicating which fringe a point belongs to). The fringe number is needed to determine the absolute height at the measurement point relative to a reference plane. A field-shifting technique (sometimes termed phase-shifting in the art) is also used for sub-fringe analysis (accurate determination of the height of the measurement point within the height range occupied by its fringe). These field-shifting methods coupled with a camera-based interferometry approach allow accurate and rapid absolute height measurement, permitting measurement to be made in spite of possible height discontinuities in the surface. The technique allows absolute height of each of the roughly 250,000 discrete points (pixels) on the sample surface to be obtained, if suitable optics, video hardware, data acquisition equipment, and software are used that incorporates the principles of moire interferometry with field-shifting. Each point measured has a resolution of approximately 1.5 microns in its height measurement.

The computerized interferometer system is used to acquire topographical data and then to generate a grayscale image of the topographical data. The grayscale image is hereinafter called "the height map". The height map is displayed on a computer monitor, typically in 256 of more shades of gray and is quantitatively based on the topographical data obtained for the sample being measured. Again, the optical system should use a 38 millimeters×38 millimeters field of view. The resulting height map for the 38 millimeters square measurement area should contain approximately 250,000 data points corresponding to approximately 500 pixels in both the horizontal and vertical directions of the displayed height map. The pixel dimensions of the height map are based on a 512×512 CCD camera which provides images of moire patterns on the sample which can be analyzed by computer software. Each pixel in the height map represents a height measurement at the corresponding x- and y-location on the sample. In the recommended system, each pixel has a width of approximately 70 microns. The z-direction height measurement must have a nominal accuracy of better than about 2 microns and a z-direction range of at least 1.5 mm. (For further background on the measurement method, see the CADEYES Product Guide, Medar, Inc., Farmington Hills, Mich., 1994, or other CADEYES manuals and publications of Medar, Inc.)

The CADEYES system can measure up to 8 moire fringes, with each fringe being divided into 256 depth counts (sub-fringe height increments, the smallest resolvable height difference). There will be 2048 height counts over the measurement range. This determines the total z-direction range, which is approximately 3 millimeters in the 38 millimeters field-of-view instrument. If the height variation in the field of view covers more than eight fringes, a wrap-around effect occurs, in which the ninth fringe is labeled as if it were the first fringe and the tenth fringe is labeled as the second, etc. In other words, the measured height will be shifted by 2048 depth counts. Accurate measurement is limited to the main field of 8 fringes.

Acquiring Data for a Tissue Sample

The moire interferometer system, once installed and factory calibrated to provide the accuracy and z-direction range stated above, can provide accurate topographical data for materials such as bath tissue. The accuracy of factory calibration can be confirmed by performing measurements on surfaces with known dimensions such as calibration samples for common commercial thickness gauges. Measured thickness should consistently be within 4 percent of the nominal calibration standard and preferably within 2 percent. In performing a test, a sample of tissue is maintained for at least 24 hours under TAPPI conditions (73° F., 50% relative humidity). The sample must be placed flat on a surface lying aligned or nearly aligned with the measurement plane of the instrument and should be at such a height that both the lowest and highest regions of interest are within the measurement region of the instrument. The sample is not stretched or compressed, but lies on the sample holder without being under tension, allowing the surface of the sheet to be in a relatively natural state as would be encountered when viewed during consumer use. The sheet also should not be treated with coatings or other treatments that would significantly perturb the structure of the surface.

Once the sample is properly placed, data acquisition is initiated using the PC software and a height map of 250,000 data points is acquired and displayed, typically within 30 seconds from the time data acquisition was initiated. (Using the CADEYES® system, the "contrast threshold level" for noise rejection is set to 1, providing some noise rejection without excessive rejection of data.) Data reduction and display are achieved using CADEYES® software for PCs, which incorporates a customizable interface based on Microsoft Visual Basic Professional for Windows (version 3.0). The Visual Basic interface allows users to add custom analysis tools, such as the embossing depth procedures described below.

Figure 4:
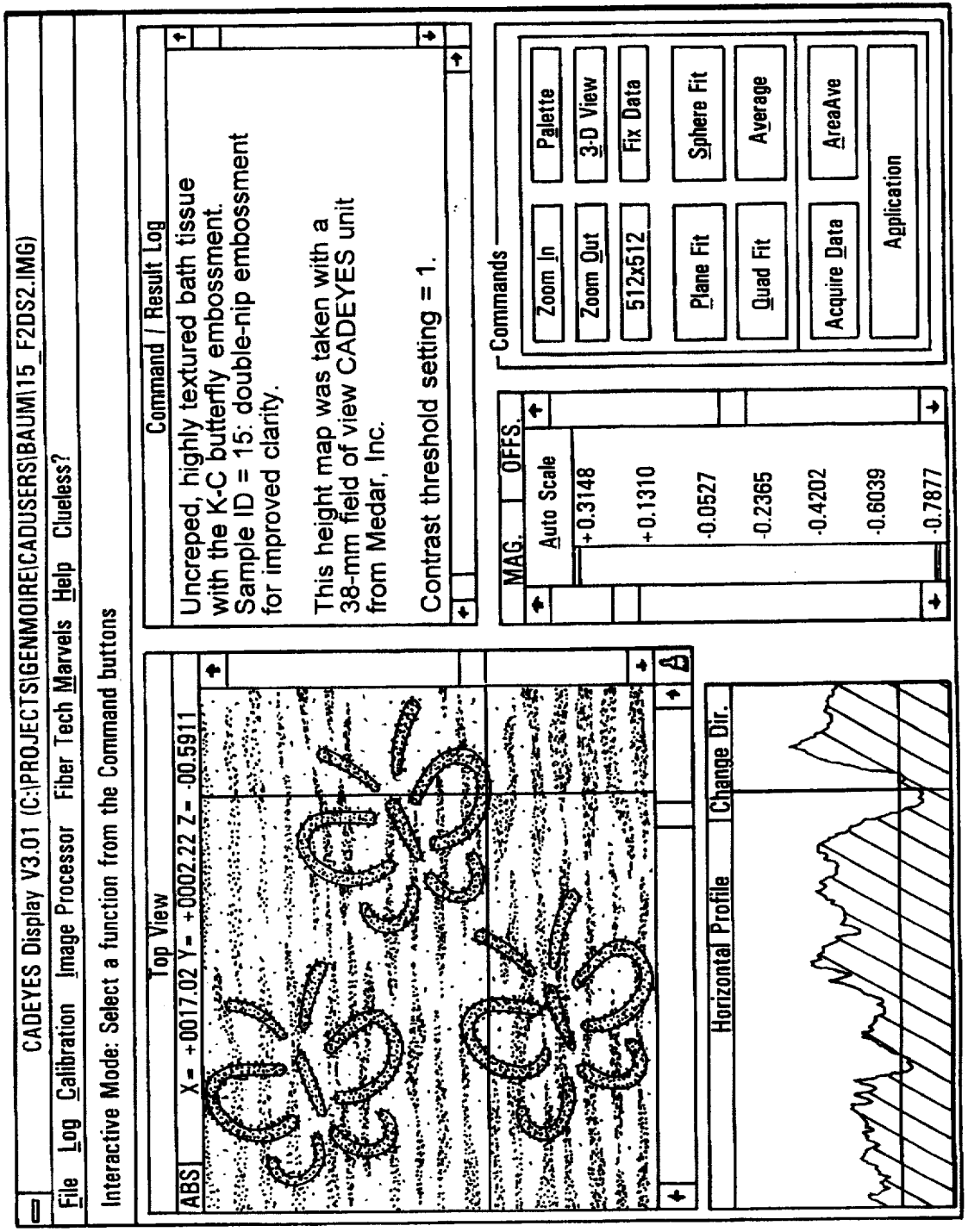
FIG. 4 is a print-out of the main CADEYES® window, illustrating the height map of a tissue in accordance with this invention.

The height map should contain regions that are embossed as well as regions that are not embossed. Typical embossments are less than 38 millimeters in extent and can be contained completely on a single height map. If the embossment is larger, separate regions can be analyzed separately and the results combined to provide data for a single embossment. FIG. 4 shows a printout of the main CADEYES® window from the commercial PC software by Medar, Inc., showing a height map of an uncreped bath tissue that has been embossed with a butterfly pattern using double-nip embossing. The scale in the lower middle of the window shows the relationship between grayscale intensity and height (all heights are in units of millimeters and are heights relative to a reference plane that is defined by the optical hardware and by system calibration). On the grayscale image displayed on the monitor, the darker the color, the lower the measured surface. A 2-dimensional profile is displayed in the lower left-hand corner of the window. This is the height profile along the horizontal crosshair line on the height map.

It is natural for some parts of the sheet to be wavy due to the embossment itself. The sheet should not be stretched or pressed flat, but should be simply placed flat under the optics on a flat surface. The natural waviness of the sheet may slightly affect the Mean Embossing Clarity results and may diminish the measured difference between embossed and unembossed areas, but this is appropriate. Embossments are viewed by the eye when the sheet is in its natural state, not when it is stretched or artificially forced to be flat. Some embossments impart waviness to the sheet around the embossment in a manner that can optically interfere with the perceived clarity of the embossment. This effect is included to a degree in the present test method, although it is believed to have only a minor effect on mean values, while natural sheet waviness should increase the standard deviation of embossing measurements.

The Embossing Clarity Measurement

The principle of embossing clarity measurement with topographical data is to compare localized regions of the embossment with nearby unembossed regions to calculate a characteristic height difference between the embossed and unembossed regions. This needs to be done in a reproducible manner, using consistent methods to enable comparison of embossing strategies.

In order to assist in understanding the following discussion, the definition of several terms may be helpful at this point for reference.

A "profile line" is a line segment drawn on a topographical height map in order to select a region of the data set from which a two-dimensional height profile will be extracted. For example, multiple straight profile lines are shown on the height map in FIG. 5. The data corresponding to the height values of pixels on those lines can be used to provide a height profile for that profile line, as described below.

A "profile" or "height profile" is a two-dimensional representation of the surface elevation along a profile line. For example, two height profiles are shown in rectangular picture boxes below and to the right of the height map in FIG. 5. The profile shown below the height map was derived from the long horizontal profile line on the height map, while the profile to the right of the height map derives from the long vertical profile line on the upper left quadrant of the height map in FIG. 5.

The "local embossing depth" of a profile is a measure of the difference in average height between a profile inside an embossment and typically two surrounding profiles from profile lines near the profile line in the embossment but lying outside the embossment. Where possible, the profile line in the embossment will be surrounded by two parallel profile lines outside the embossment. In cases where the embossment is wider than about 3 millimeters, the profile lines in the embossment will be drawn near the boundaries of the embossment, making it unfeasible for each profile line in the embossment to be surrounded by nearby lines in the unembossed area. In that case, only one nearby profile line outside the embossment is needed for comparison with a profile line in the embossment. The comparison in height between the profile line in the embossment and the lines or line outside the embossment is performed by taking the mean height of the profile from the profile line in the embossment and subtracting it from the mean height of the nearby height profiles from the profile lines or line in the unembossed area. (Missing data and obvious optical noise should not be included in performing the measurements, of course). The height difference is the local embossing depth of the profile in the embossment (or simply local embossing depth). (In FIGS. 6A and 6B, local embossing depths are labeled as "Mn.Diff").

The "placement-specific embossing depth" is a measure of the characteristic embossing depth of a profile from a set of profile lines that represent an entire embossment pattern. Using an ensemble of profile lines lying within an embossment, said profile lines adequately representing the ensemble as described in the specification, the local embossing depth is calculated for each profile line in the ensemble and the median of those values is taken as the placement-specific embossing depth. Because the median value is used, this parameter could be termed the "median-based placement-specific embossing depth", though simply "placement-specific embossing depth" will be used.

The "embossing clarity" is the maximum placement-specific embossing depth obtained from a set of nine ensemble placements for a single embossment. When the ensemble of profile lines is placed over an embossment area on the height map, computer software is used to adjust the location of the ensemble by shifting the entire ensemble by up to 1 pixel either to the left or right and up to 1 pixel either up or down, resulting in 9 different placements to be considered; this is done to reduce the effect of operator variability in placing an ensemble over an embossment. For each placement, the placement-specific embossing depth is obtained. The maximum value of the 9 placement-specific embossing depths is taken as an indication of the distinctness of the embossment and is termed the "embossing clarity", which is the primary variable considered in describing the success of the invention in improving clarity of embossing. (In FIGS. 6A and 6B, embossing clarity values are labeled as "MaxMed").

When multiple embossments from a single sample type have been analyzed for embossing clarity using the methods described herein, the mean value of "embossing clarity" from the multiple embossments so analyzed is defined as the "Mean Embossing Clarity."

The "mean-based placement-specific embossing depth" is obtained in a manner identical to the (median-based) placement-specific embossing depth described above except that the mean value (not the median) is taken from the multiple local embossing depths of the multiple profiles in an ensemble of profiles in an embossment.

The "mean-based embossing clarity" is obtained in the same manner as the standard (median-based) embossing clarity definition above, except that mean-based placement-specific embossing depths are obtained from each of the nine ensemble placements instead of (median-based) placement-specific embossing depths. (In FIGS. 6A and 6B, mean-based embossing clarity values are labeled as "MaxMn").

The "mean-based mean embossing clarity" is obtained in the same manner as the standard (median-based) Mean Embossing Clarity definition above, except that mean-based embossing clarity values are obtained (rather than embossing clarity values, which are median-based) from each embossment measured. The mean of those multiple mean-based embossing clarity values is the mean-based mean embossing clarity.

Returning from the definitions to the discussion for measuring embossing clarity, the recommended procedure is to sample representative 2-dimensional height profiles from within the embossment, in such a way that much of the embossment is represented by selected profile lines, and to compare the height profile from each selected profile line or region with nearby profiles or regions outside the embossment. Pairwise comparisons are conducted for the embossed profiles or regions and the neighboring unembossed profiles or regions in order to provide a mean height difference (the "local embossing depth") for that portion of the embossment. This is done for multiple portions of the embossment, providing data that can be used to obtain a median and a mean from the set of local embossing depths for the various discrete segments of the embossment.

On a 512 pixel×512 pixel grayscale height map, a series of line segments should be selected from which height profiles along those lines can be extracted. This is conveniently done with Microsoft Visual Basic Software (version 3.0) for Windows. For the Kimberly-Clark butterfly design used in the tests of the present work, customized software was written to produce an ensemble of 11 line segments that could all fall within the embossed butterfly region as long as the sample was aligned nearly rectilinearly with the instrument during measurement. Once an ensemble has been defined, preferably using height maps with clearly visible embossments to establish an ensemble layout (the representation of the embossment), the same ensemble should be used for all comparisons between sheets having that embossing pattern. The software should dynamically draw and redraw the ensemble of 11 lines relative to the position of the cursor (controlled by a mouse) on the height map. The ensemble of lines follows the cursor until the user clicks the mouse or issues a keyboard command, at which time the ensemble is fixed onto the height map and the appropriate profile data are extracted from the topographical data set for processing.

The method of graphically placing an ensemble of line segments on the height map allows the user to use the mouse to vertically and horizontally translate the group of line segments (11 for the butterfly representation, or whatever number of line segments is appropriate for the embossment in question) on the height map until they are superimposed over the embossment. The ensemble is "rigid" and cannot be rotated, stretched, or adjusted except via lateral (vertical and horizontal) translation, requiring samples to be reasonably well aligned prior to measurement to ensure that the ensemble pattern will be able to correspond well to embossments on the sample. In using the ensemble of 11 lines specific to the butterfly pattern discussed above, clicking the mouse causes 11 2-dimensional height profiles to be extracted from topographical data set, corresponding to the data points most nearly on the 11 lines segments drawn on the image. In addition, parallel to each line segment in the embossment are two other line segments for which data are also extracted from the topographical data set that was used to produce the displayed height map. (Preferably the two external line segments parallel to a line segment internal to the embossment have the same length as the corresponding internal line segment.) Details of data extraction to obtain 2-dimensional height profiles along the placed profile lines on the height map are offered below.

Figure 5:
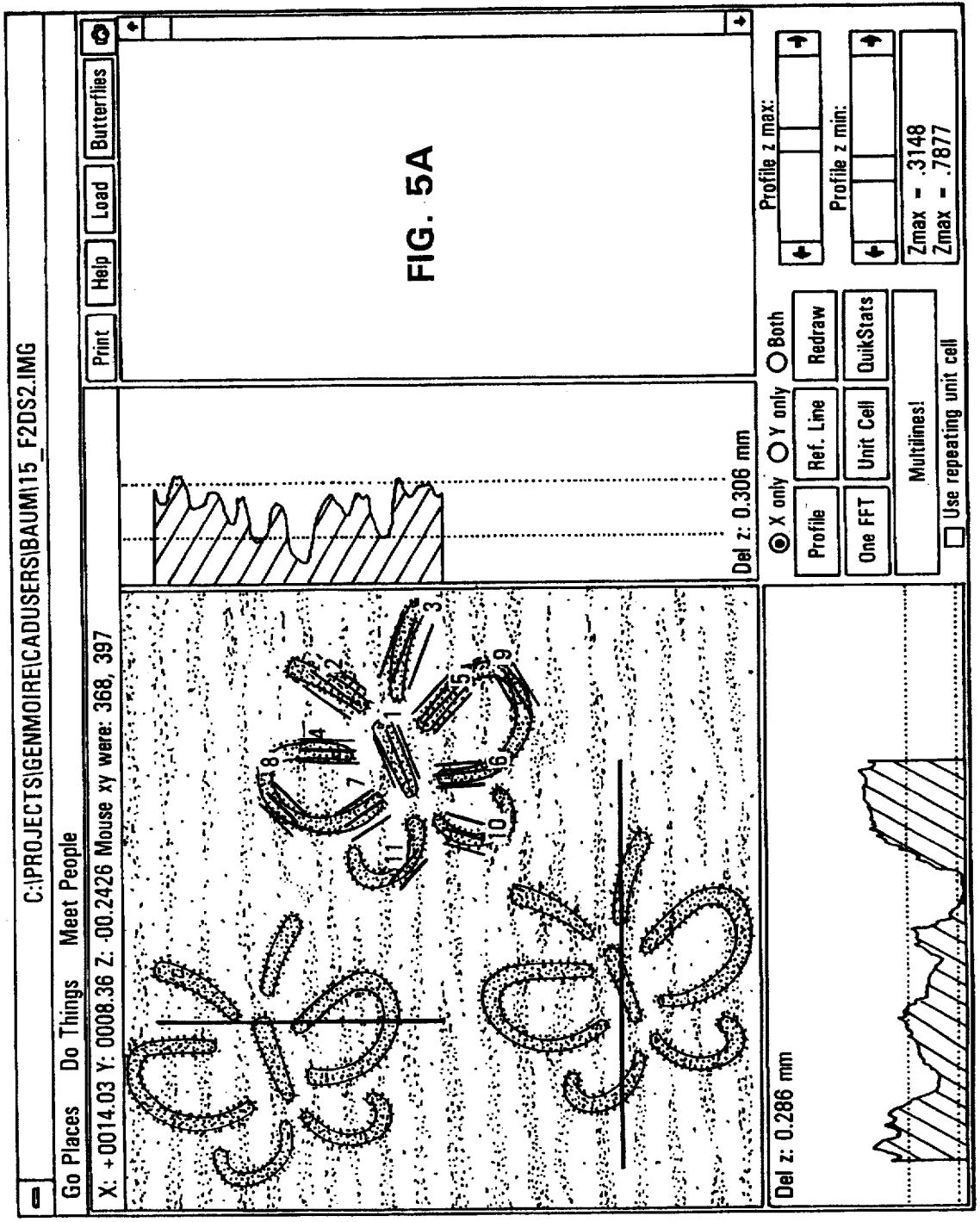

An example of this approach is shown in FIG. 5, where a larger display (full 512×512 pixels) of the same height map in FIG. 4 is presented. This window (a customized Visual Basic form, such as can be produced by one skilled in the art, though most conveniently done by adopting existing software tools in the CADEYES software system) also shows two profiles from two arbitrary profile lines drawn on the height map (profile lines can be drawn in any orientation on the height map shown on the custom form, not just in the vertical or horizontal directions as is the case for the original CADEYES software). The profile displayed to the right of the height map is the 2-dimensional height profile along the profile line passing vertically through the uppermost butterfly embossment. The profile in the lower portion of the window corresponds to the profile line drawn horizontally through the lowest butterfly. Representative dimensions are labeled on both profile boxes (0.306 millimeter and 0.286 millimeter, respectively, showing the distance between the marked lines on each height profile).

The black lines over the butterfly on the right side of the height map comprise the ensemble of 11 line groups mentioned above. In addition, each of the lines over the butterfly embossment is surrounded by a pair of parallel lines, forming a group of three lines. The middle line of each group of three parallel lines should lie within the embossment, while the other two should lie outside. For other embossment patterns, multiple line segments should be used to represent most of the embossment, as will be discussed below.

The embossments measured should be produced from elements of common height on the embossing roll, otherwise it may be invalid to combine embossments produced by elements of differing heights. Normally the embossment of interest will be produced by elements of common heights. If not, the embossments produced by the elements of greatest height should be measured independently of other embossed regions.

To obtain the "placement-specific embossing depth" for a particular embossment on a tissue sample, the average height of each line segment within the embossment is compared to the average height of the two parallel nearby line segments outside the embossment. For a particular group of three parallel profile lines, the local embossing depth is the average of the two average profile heights for the external lines minus the average profile height of the internal line (the line within the embossment). The placement-specific embossing depth for the particular placement of profile lines on that embossment is the median of the multiple local embossing depths from the multiple line segments used to represent the embossment.

In using this approach, the user must choose where to place the ensemble of line segments over the height map to best fit within the embossment. A complication arises due to the subjective decision of the user as to where the best placement of a given representation is. To reduce the uncertainty caused by placement of the ensemble of profile lines on the image, the software for embossing analysis treats the user-selected placement point (the pixel coordinates of the cursor location on the height map when the mouse is clicked) as the central pixel of a 3×3 pixel grid. The software then considers, in succession, each of the nine pixels in that grid as if that pixel had been the clickpoint (the place where the user had clicked), moving the entire ensemble of lines appropriately for each pixel. For each of the nine automatically considered placements of the ensemble, 11 local embossment depths (for the present case of 11 profile lines representing a butterfly pattern) are determined and the median, mean, and standard deviation of those 11 values are reported on a spreadsheet grid in another Visual Basic form (or, alternatively, in a dedicated spreadsheet program). This is done for all nine ensemble placements for the 3×3 grid of clickpoint pixels. The median value for each of the 9 placements is a placement-specific embossing depth.

An example is shown in the table of FIGS. 6A and 6B, where typical output data are displayed. The data in FIGS. 6A and 6B were automatically generated from the height map shown in FIG. 5 for the placement of the butterfly ensemble shown therein. The clickpoint was at the pixel location I=349, J=235, where I is the number of pixels over from the left edge and J is the number of pixels down from the top edge of the height map. Data for each of the eleven lines in the butterfly representation are shown in separate columns. Rows 3 through 6 of the table give the pixel coordinates for the endpoints of each of the eleven lines for the ensemble as placed at the original clickpoint (at I=348, J=234), which is also equivalent to the base (the lower left hand end) of the line segment running in the body of the butterfly (line segment 1). Thus, for each of the 11 profile line segments in the butterfly representation, I1 and J1 define the pixel location of one endpoint, and I2 and J2 give the other endpoint.

In FIGS. 6A and 6B, 9 sets of embossing depth data are presented for each ensemble placement. The clickpoint (I=348, J=234) is taken as the central pixel, but I values from 347 to 349 are considered as are J values from 233 to 235 as the effective clickpoint is scanned across the 3×3 pixel area from (I=347, J=233) to (I=349, J=235). The entire ensemble is translated appropriately and statistics are calculated for each placement. For examples, rows 7 through 10 of FIG. 6A show results for an effective clickpoint of (I=347, J=233). "EmbAvg" in row 7 is the average height of the profile line for each of the 11 lines considered in the butterfly ensemble. "Ext1" and "Ext2" are mean heights along each of the two external, parallel lines near the line in the embossment. "MnDiff" is the difference in height between the average of the two external profile lines and the profile line in the embossment, or MnDiff=0.5*(Ext1+Ext2) −EmbAvg, which gives the local embossing depth. A positive value indicates that the profile in the embossment was lower, on the average, than the profiles from the surrounding area. The median, mean, and standard deviation of the 11 local embossing depth values are reported in row 10 at the right hand side of the table. The median value is considered more representative than the mean in this application because it is less sensitive to outliers and more likely to return a "typical" value of embossing depth. Thus, for the placement of the butterfly ensemble at pixel location I=347, J=233 (i.e., the base of line segment 1 begins at that point), the characteristic "placement-specific embossing depth" is 0.165 millimeter. The mean of the local embossing depth values is 0.151 millimeter for that ensemble placement; this parameter is defined as the "mean-based placement-specific embossing depth".

In total, nine distinct ensemble placements are considered, with results shown in FIGS. 6A and 6B. Of the nine placement-specific embossing depths (median MnDiff values) listed, the maximum value is taken as the "embossing clarity" for the embossment being considered (in this case, the rightmost complete butterfly in the height map shown FIGS. 4 and 5). In FIGS. 6A and 6B, the embossing clarity is 0.165 millimeter and is listed under the label "MaxMed" (the maximum of the medians) in Row 52, in the same column as the median MnDiff values. Alternatively, though not equivalently, one could consider each of the 11 line segments separately and take the maximum of the 9 MnDiff values listed in the respective column, and then take the median of the 11 maximum values. Row 52 in FIG. 6B lists the maximum MnDiff value for each line segment of the butterfly representation. The median of these maxima is also 0.165 millimeter and is listed in Row 52 under the label "MedMax" (median of the maxima). In general, "MaxMed" and "MedMax" will have similar but not identical values. "MaxMed" will be used for embossing depth assessment.

For comparison, also listed in Row 52 of FIG. 6B is "MaxMn", the maximum of the 9 placement-specific means of MnDiff (in other words, "MaxMin" is the maximum of the 9 mean-based placement-specific embossing depths, or simply the mean-based embossing clarity") and "MnMax," the mean of the 11 maxima for lines 1 through 11 in Row 52. The last pair of numbers in Row 52 are the I and J pixel locations of the original clickpoint.

Taking the maximum of the 9 median values in FIGS. 6A and 6B is desirable because we are interested in optimizing the location of the embossment representation (the ensemble of profile line segments) in order to determine the contrast in height caused by embossing. Some placements may put ensemble lines that should be in the embossment partially off the embossed area, giving artificially low embossing depths. A mean value is inappropriate, whereas a maximum value captures some of the contrast that exists and that could assist visual discernment of the embossed pattern. In some cases, the operator may seem to have a choice of many adequate clickpoints to place the ensemble, these adequate locations covering more than a 3×3 grid of pixels. In such cases, the operator may conduct the automatic 3×3 scan at different locations and report the maximum of the several "MaxMed" values, though such a procedure should normally not be necessary.

Note that the procedures above provide a single embossing clarity value for a single embossment. Embossing clarity analysis of multiple embossments (and multiple samples) must be performed to obtain statistically significant measures of embossing clarity. By obtaining measurements for multiple embossments from a given product, an overall average can be determined for embossing clarity, resulting in the "Mean Embossing Clarity" for that product.

Defining Representations of Embossments (Ensembles of Profiles) for Data Extraction The details of the strategy for extracting data from an embossment, as presented below, will be directed toward the case of embossments with contiguous embossed regions extending more than about 2 millimeters in length (as is the case for typical embossment patterns such as butterflies, flowers, and other objects). Smaller embossments, as may be found in patterns or textures created by discrete pins, can be treated using similar principles, although the data to be extracted from the embossment for comparison with surrounding unembossed areas will not be obtained from profile lines in the embossment, but from a representative area selected inside the embossment to represent to the typical depth of the embossment.

For embossments regions less than 3 millimeters in width, a single profile line running inside the embossment is considered adequate to represent the embossment across its width (profile lines should generally be in the base of the embossment and not on the edge itself where a steep gradient in height may exist). Sufficient line segments inside the embossment should be selected to cover over 40% (and preferably 50% or more) of the embossment. For embossment zones broader than 3 millimeters, profile lines within 1.5 millimeters of the edge should be drawn around the periphery, providing total profile line length to represent at least 40% of the perimeter, as described below.

To ensure that sufficient lines have been drawn to represent at least 40% of the perimeter of the object, one may first estimate the line length required to represent 100% of the perimeter. This is done by drawing some combination of polygons and lines inside each distinct embossed region of a representative embossment pattern such that each point on the perimeter lies no more than 1.5 millimeters from a line or an edge of a polygon in the embossment. Lines and polygons in the full representation should be connected to form a continuous pathway between all lines in a single embossed region. (For structures such as circles or ovals that may not offer obvious pathways along which to draw lines, or for structures with maximum dimensions less than 3 millimeters, line segments should contact the perimeter at opposite ends of the embossment to ensure that the line length is at least as great at the major dimension of the embossed region. For example, a 2 millimeters circle could be fully represented by a diameter line, or an oval could be fully represented with line segments that begin and end at opposite endpoints along the major axis.) Once a full representation has been established, the total length of the lines and polygon sides are added. That sum, multiplied by 0.4, indicates the minimum total line length required to represent the embossment depth with discreet profile lines. For ease of subsequent analysis, the profile lines for embossing depth measurement should be of similar length, with the shortest line being no less than 75% the length of the longest line in the set.

Figure 7B:
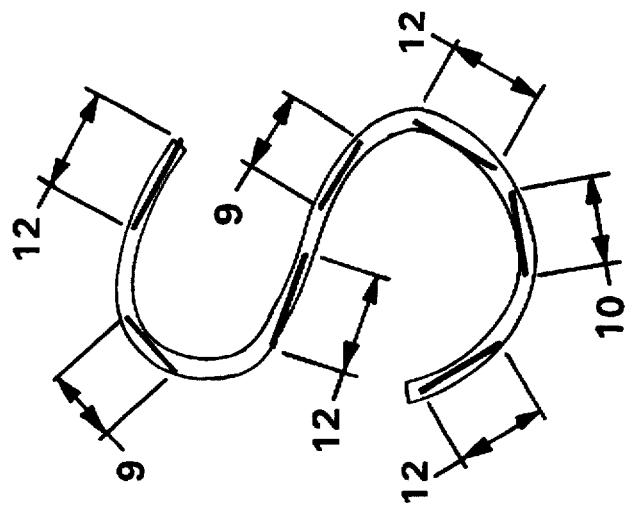
FIGS. 7A and 7B illustrate the selection of representative profile lines for a hypothetical embossment.
Figure 7A:
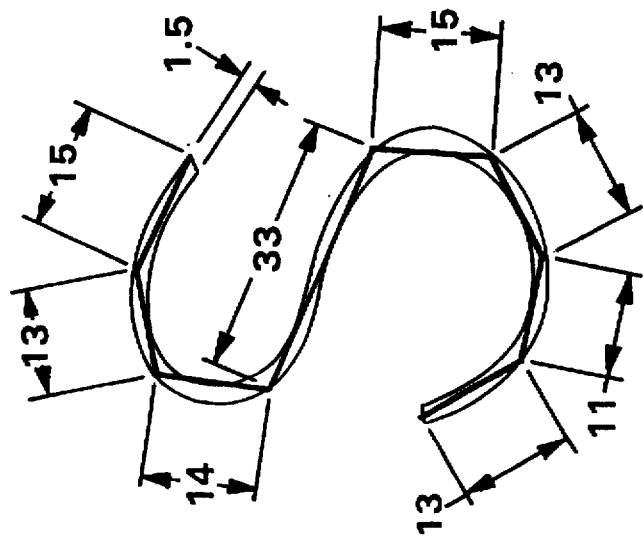

By way of illustration, the method of selecting representative profile lines on an embossment is shown in FIGS. 7A and 7B for a hypothetical embossing pattern similar to the letter "S." FIG. 7A shows a possible full representation of the pattern, with internal lines drawn such that no point on the perimeter of the embossment is further than 1.5 millimeters away from an internal line (defined as a manually added line inside the embossment). The length in millimeters of each internal line in the full representation is shown in the figure and these lengths are listed in Table 1 below. The sum of the line lengths is 127 mm. A minimum partial representation should then have 0.4*127=50.8 millimeters total line length. A reasonable representation for measurement is shown in FIG. 7B, where 7 line segments have been drawn which roughly define the basic shape of the embossment. The line segments, listed and summed in Table 1, have a total length of 76 millimeters, suitably exceeding the minimum of 50.8 millimeters.

TABLE 1

| (Segment Lengths (millimeters)) | |
|---|---|
| Full representation | Partial representation |
| 15 | 12 |
| 13 | 9 |
| 14 | 12 |
| 33 | 9 |
| 15 | 12 |
| 13 | 10 |
| 11 | 12 |
| 13 | |
| Total: 127 min length: 50.8 | Total: 76 |

While most embossing patterns consist of segments no wider than 3 millimeters, it is instructive to consider exceptions. For example, FIGS. 8A, 8B and 8C show possible treatments of circular regions. The 5 millimeter circle in FIG. 8A has a minimal full representation formed by a 2 millimeters circle (which is 1.5 millimeters away from points on the 5 millimeters circle) plus two line segments along the diameter of the circle to provide attachment to the perimeter at two opposing points. The length of the minimal full representation is roughly 9.3 millimeters. A suitable measurement representation is given by a hexagon with line segments 2 millimeters in diameter, for a total length of 12 millimeters. However, given that the intent of the procedure is to adequately and conveniently represent a significant portion of the embossment boundary, the use of the hexagon as a measurement representation would be reasonable and more convenient that using many short line segments lying on the internal circle of the minimal full representation. The objective is to capture depth differences between the embossment and the surrounding unembossed paper, using reasonable and fair procedures to represent a significant portion of the perimeter. Depth differences near the border of the embossment are especially desirable to measure, for this is most influential in providing visual contrast.

A further example is provided in FIGS. 8B and 8C, which deal with a 3 millimeters circle. In this case, a minimal full representation is obtained with a chord 3 millimeters in length. Technically, a marginally suitable measurement representation could then be obtained with a portion of the diameter 1.2 millimeters long, but a more suitable measurement representation may be similar to that shown in FIG. 8C, where two chords have been used with a combined length greater than the minimal full representation.

Finally, FIGS. 9A and 9B show an example of a complex pattern having thin and thick regions. A suitable full representation is shown in FIG. 9A, with a reasonable measurement representation in FIG. 9B.

For a given embossing pattern, a reasonable and suitable measurement representation should be selected and established a priori, before measurements are made. Once it has been selected, it should be used consistently in evaluating the embossing efficacy of a various embossing methods relative to controls.

The method above is likely to yield a conservative estimate of the depth differences caused by embossing. For example, some regions of the tissue shown in FIGS. 4 and 5 have depths that appear to be 0.2 to 0.4 millimeter deeper than the immediately surrounding sheet, yet the average depth of the embossment relative to the average depth of the surrounding sheet may only reveal values of 0.15–0.2 millimeter due to natural variation in the surface and because of the background texture of the molded uncreped through-air-dried sheet. For this reason the representation must be selected to define the basic shape of the embossing area and not simply designed to capture only the areas of highest contrast. Once an embossing representation is selected, it should be applied unchanged to all samples studied.

In addition to the embossing representation, line segments (or areas) should be selected to enable comparison of the each segment in the representation to the unembossed regions of the sheet. For each segment or region of the embossment's representation, at least as many height data points from outside the embossment should be extracted for comparison. When possible, it is desirable to compare each segment of the representation to profiles extracted from two nearby parallel lines on the unembossed portion of the sheet, said parallel lines running along both sides of the embossment, as shown in FIG. 3, where each set of three parallel lines consists of a central line from the butterfly representation surrounded by two parallel lines outside the embossment.

Extracting Height Data from a Height Map of Embossment for Embossment Depth Analysis Once an ensemble of lines representing an embossment has been defined, with the associated ensemble of lines (or areas, if needed) representing portions of the unembossed sheet, and once these ensembles have been suitably placed on the height map, the topographical data for each line segment (or area) need to be extracted from the topographical data set for analysis. While the procedure may be straightforward to those skilled in the art, it is described here in detail for clarity. Along a profile line of arbitrary orientation, the number of data points to be extracted for that profile corresponds to the maximum number of pixels traversed in either the vertical or horizontal directions between the two endpoints. For example, a line from one corner of a 512×512 pixel height map to the diagonally opposite corner will result in 512 data points being extracted. (The line itself is longer by a factor of √2−1 than 512 pixels are wide or tall, but the characteristic length traversed across the individual pixels in the image is also longer than the pixel width by the same factor.) Thus, in extracting data from an arbitrary line drawn on a height map, we must first determine if more pixels are traversed in the horizontal or vertical directions; the direction with the most pixels will be the scan direction, and the number of pixels in the scan direction will be the length of the data vector (an array) that will be filled with a series of height values extracted from the topographical data set. A simple linear equation is used to relate I coordinates (horizontal pixels from the left edge) to J pixels (pixels down from the top edge of the height map). For each pixel in the scan direction, the linear equation is used to determine the value of the other coordinate that most nearly lies on the user-selected line. Knowing the I and J coordinates of a pixel, the corresponding height value is extracted in the CADEYES software using the "ij2point3D" command, issue a Visual Basic call to compiled code from Medar, Inc. This procedure is used to create a list of points in the topographical data set that lie along the profile line. The list is then processed with the "CalcStats" command to return a mean and other statistics. An example of the process is shown below in an extract from a custom Visual Basic software module for embossing analysis.

In the following segment of code, the endpoints of a line segment are at pixel locations (i1, j1) and (i2, j2). Displayimage is a reference to the entire topographical data set; pnt refers to a single point in that 3-D data set, with pnt itself having x,y, and z values; mylist is the list of points extracted along a profile line; Addpoint is a call to a procedure that adds specified points to the point list; and ij2point3d returns the topographical point pnt from displayimage for a specified height map pixel coordinate.

Extracted points (excluding missing data) are used to fill a point list that is then processed by Medar's CalcStats call—which has been shown to give same results as manual calculation of means, standard deviations, etc. Points are extracted by scanning in the direction with the most pixels. The other coordinate location is determined linearly, giving the pixel closest to the line.

```
If Abs(i1 - i2) > Abs(j1 - j2) Then
    A1 = i1: A2 = i2         'A1 and A2 are coordinates
of the direction 'with the most span first
    B1 = j1: B2 = j2
    ScanX = True
Else
    B1 = i1: B2 = i2
    A1 = j1: A2 = j2
    ScanX = False
End If
If A2 > A1 Then
    DeltaStep = 1
ElseIf A2 < A1 Then
    DeltaStep = -1
End If
If ScanX = True Then
'Case 1: major axis is in the x-direction
    For Astep = A1 To A2 Step DeltaStep
        Bcoord = B1 + Int((Astep - A1) * (B2 - B1 + .0001) / (A2 -
A1) +     .499) 'the linear formula used to relate one
'coordinate to the other along the line
        ij2point3d pnt, displayimage, Astep, Bcoord
'Astep must be an X pixel, Bcoord a Y pixel
        Addpoint mylist, pnt
    Next Astep
Else 'ScanX is false: the following code is same as above
'except in the ij2point3D call,
'where Astep and Bcoord are switched, reflecting the fact that Astep
'is now a Y-pixel coordinate and Bcoord is an X-pixel coordinate.
'Case 2: major axis is in the y-direction
    For Astep = A1 To A2 Step DeltaStep
        Bcoord = B1 + Int((Astep - A1) * (B2 - B1 + .0001) / (A2 -
A1) + .499)
        ij2point3d pnt, displayimage, Bcoord, Astep
        'Astep must be a Y pixel, Bcoord an X pixel
        Addpoint mylist, pnt
    Next Astep
End If
CalcStats avgpt, devPT, minmpt, maxmpt, mylist
```

Further Clarification: Selected Code for Defining and Analyzing the Butterfly Embossment Though it is not necessary for those skilled in the art, the following code segments are provided for further clarification and to facilitate those wishing to reproduce aspects of the teachings herein using a Visual Basic interface. The code is not complete and refers to some calls and variables not listed or described in detail here. The intent is to provide optional guidance and clarification of the strategy given above. The following code segments are used in defining the butterfly ensemble and the parallel line segments, from which data are extracted as described above to produce results such as those in FIG. 6. The first segment shows how an array of pixel locations is filled when the user clicks on the "Butterfly" button shown in FIG. 5. These pixel locations correspond to the locations of lines once drawn on an actual butterfly embossment that was used to define the representation for subsequent analysis. These pixel locations will later be made relative to the mouse location by subtracting the pixel locations of the base of line segment (see below).

Partial script from the Butterflies button, activated upon clicking

First fill the butterfly ensemble locations for the 11 line 'segments in the representation:
Butterx1(1)=165: Buttery1(1)=388:
Butterx2(1)=214:
Buttery2(1)=366
 Butterx1(2)=232: Buttery1(2)=342: Butterx2(2)=259: Buttery2(2)=303
 Butterx1(3)=250: Buttery1(3)=372: Butterx2(3)=302: Buttery2(3)=391
 Butterx1(4)=197: Buttery1(4)=343: Butterx2(4)=200: Buttery2(4)=294
 Butterx1(5)=217: Buttery1(5)=394: Butterx2(5)=249: Buttery2(5)=425
 Butterx1(6)=180: Buttery1(6)=409: Butterx2(6)=181: Buttery2(6)=445
 Butterx1(7)=150: Buttery1(7)=356: Butterx2(7)=135: Buttery2(7)=332
 Butterx1(8)=225: Buttery1(8)=473: Butterx2(8)=260: Buttery2(8)=453
 Butterx1(9)=142: Buttery1(9)=299: Butterx2(9)=170: Buttery2(9)=270
 Butterx1(10)=132: Buttery1(10)=414: Butterx2(10)=123: Buttery2(10)=444
 Butterx1(11)=114: Buttery1(11)=388: Butterx2(11)=92: Buttery2(11)=368

'Now fill arrays that describe the x and y increments used to make the 'parallel external lines. Each parallel line has the same coordinates as 'the line in the embossment, except that the x (or i) coordinates of line 'P has DX(P) added or subtracted, and the y (or j) coordinates of line P has DY(P) added or subtracted

DX(1)=4: DY(1)=12

DX(2)=12: DY(2)=5

DX(3)=−5: DY(3)=12

DX(4)=12: DY(4)=−2

DX(5)=−8: DY(5)=8

DX(6)=12: DY(6)=0

DX(7)=−8: DY(7)=8

DX(8)=2: DY(8)=12

DX(9)=8: DY(9)=8

DX(10)=12: DY(10)=2

DX(11)=−4: DY(11)=10

'Partial selection of code from the height map picture box, activated 'upon clicking the mouse when the ensemble is properly placed:

```
For j = 1 To ButrNum 'ButrNum is the number of line
segments – 11 for 'us
'Draw and remember the coordinates of the butterfly lines
'The multix1, etc., arrays contain pixel locations of the lines to be
'processed. For ButrNum = 11, there will be a total off 33 lines.
   multix1(j) = Butterx1(j) – Butterx1(1) + X:
      multiy1(j) = Buttery1(j) – Buttery1(1) + Y
   multix2(j) = Butterx2(j) – Butterx1(1) + X: multiy2(j) =
      Buttery2(j) – Buttery1(1) + Y
   Picture1.Line (multix1(j), multiy1(j))–(multix2(j),
      multiy2(j)),
      QBColor(14)
'Now draw and remember external lines – parallel to the butterfly
'lines
   multix1(j + ButrNum) = multix1(j) + DX(j): multiy1(j +
      ButrNum) = multiy1(j) + DY(j)
   multix2(j + ButrNum) = multix2(j) + DX(j): multiy2(j +
      ButrNum) = multiy2(j) + DY(j)
   Picture1.Line (multix1(j + ButrNum), multiy1(j + ButrNum))–
(multix2(j +
      ButrNum), multiy2(j + ButrNum)), QBColor(10)
'Now do the symmetric external lines on the other side
'of the butterfly lines.
   multix1(j + ButrNum + ButrNum) = multix1(j) – DX(j):
      multiy1(j + ButrNum +
      ButrNum) = multiy1(j) – DY(j)
   multix2(j + ButrNum + ButrNum) = multix2(j) – DX(j):
      multiy2(j + ButrNum + ButrNum) = multiy2(j) – DY(j)
   Picture1.Line (multix1(j + ButrNum + ButrNum),
      multiy1(j + ButrNum + ButrNum))–(multix2(j +
      ButrNum + ButrNum),
      multiy2(j + ButrNum + ButrNum)), QBColor(11)
   Next j
WaitPointer True
Numlines = ButrNum 'We just show the butterfly lines on
      'the Grid.
Lastline = Numlines
LoadLinesToGrid
'Writes line coordinates on a grid on a form called Multigrid.
The grid itself is named FTgrid.
   For jj = 0 To 8
   Multigrid!FTgrid.Row = 5 + 5 * jj
   Multigrid!FTgrid.Col = 0
   Multigrid!FTgrid.Text = "EmbAvg"
   Multigrid!FTgrid.Row = 6 + 5 * jj
   Multigrid!FTgrid.Text = "Ext1"
   Multigrid!FTgrid.Row = 7 + 5 * jj
   Multigrid!FTgrid.Text = "Ext2"
   Multigrid!FTgrid.Row = 8 + 5 * jj
   Multigrid!FTgrid.Text = "Mn.Diff"
   Next jj
   Multigrid.Show 'Displays a spreadsheet-like form
      'Sum = 0
      rowinc = −1
   For jj = −1 To 1
   For ii = −1 To 1
      rowinc = rowinc +1
      For j = 1 To ButrNum
'CADEYES stats extracts data for the line segments and
'ultimately issues the CalcStats command
         CADEYESStats multix1(j) + ii, multix2(j) + ii,
multiy1(j) + jj,
            multiy2(j) + jj, Ra, flatness, avgEmbossed, minm,
maxm, dev
         CADEYESStats multix1(j + ButrNum) + ii,
            multix2(j + ButrNum) + ii,
            multiy1(j + ButrNum) + jj, multiy2(j + ButrNum) + jj,
            Ra,
            flatness, avgOut1, minm, maxm, dev
         CADEYESStats multix1(j + ButrNum + ButrNum) + ii,
multix2(j + ButrNum +
            ButrNum) + ii, multiy1(j + ButrNum + ButrNum) + jj,
```

```
    multiy2(j +
    ButrNum + ButrNum) + jj, Ra, flatness, avgOut2, minm,
    maxm, dev
Multigrid!FTgrid.Row = 5 + 5 * rowinc
Multigrid!FTgrid.Col = j
Multigrid!FTgrid.Text = Format$(avgEmbossed, "0.000")
Multigrid!FTgrid.Row = 6 + 5 * rowinc
Multigrid!FTgrid.Col = j
Multigrid!FTgrid.Text = Format$(avgOut1, "0.000")
Multigrid!FTgrid.Row = 7 + 5 * rowinc
Multigrid!FTgrid.Col = j
Multigrid!FTgrid.Text = Format$(avgOut2, "0.000")
Multigrid!FTgrid.Row = 8 + 5 * rowinc
Multigrid!FTgrid.Col = j
If minval(minval(avgEmbossed, avgOut1), avgOut2) <-
    100 Then
        Multigrid!FTgrid.Text = "NA"
Else
        Multigrid!FTgrid.Text = Format$((avgOut1 +
        avgOut2) / 2 - avgEmbossed, "0.000")
End If
Sum = Sum + (avgOut1 + avgOut2) / 2 - avgEmbossed
Next j
Get_MultiGrid_Stats (8 + 5 * rowinc), ii, jj'
'This call shows means, medians, etc., on the spreadsheet grid of the
'form called Multigrid.
Next ii
Next jj
For j = 1 To ButrNum
    Multigrid!FTgrid.Col = j
    For ii = 0 To 8
        Multigrid!FTgrid.Row = 8 + 5 * ii
        If Multigrid!FTgrid.Text = "NA" Then
            cells(ii) = -9999
        Else
            cells(ii) = Val(Multigrid!FTgrid.Text)
        End If
    Next ii
Multigrid!FTgrid.Row = Multigrid!FTgrid.Row + 2
Multigrid!FTgrid.Text = maxarray(cells(), 8) 'Writes
'the max of each column's MnDiff
Next j
'Now we make a list of 9 medians
'(each median is from the ButrNum [usually 11] sets of
'line segments analyzed for a given click point)
Multigrid!FTgrid.Col = 12
For ii = 0 To 8
    Multigrid!FTgrid.Row = 8 + 5 * ii
    If Multigrid!FTgrid.Text = "NA" Then
        cells(ii) = -9999
    Else
        cells(ii) = Val(Multigrid!FTgrid.Text)
    End If
Next ii
Multigrid!FTgrid.Row = Multigrid!FTgrid.Row + 2
'Now we report the maximum of the list of 9 medians
'(each median is from the ButrNum [usually 11] sets of
'line segments analyzed for a given click point)
Multigrid!FTgrid.Text = Format$(maxarray(cells(), 8), "0.000")
bsum = 0
Ncount = 0
    For j = 1 To ButrNum        'We get the list
    of each maximum of the 9 emb. depths for each set of
    line segments
        Multigrid!FTgrid.Col = j
        If Multigrid!FTgrid.Text <> "-9999" Then
            cells(j) = Val(Multigrid!FTgrid.Text)
            bsum = bsum + cells(j)
            Ncount = Ncount + 1
        End If
    Next j
'MultiGrid!FTgrid.Row = 48
Multigrid!FTgrid.Col = 13         'Next we get the median of
'the maxima for each of the ButrNum sets of line segments
Multigrid!FTgrid.Text = Format$(median(cells(), Ncount), "0.000")
Multigrid!FTgrid.Row = Multigrid!FTgrid.Row + 1
Multigrid!FTgrid.Text = "Med. of the maxima on this row"
Multigrid!FTgrid.Col = 12
Multigrid!FTgrid.Text = "Max. of the medians in this column"
'Now also consider the 9 means listed for each of the 9
'clickpoints, and report the maximum mean:
'Now we make a list of 9 medians
'(each median is from the ButrNum [usually 11] sets of
'line segments analyzed for a given click point)
Multigrid!FTgrid.Col = 13 'where the means are— column 13
For ii = 0 To 8
    Multigrid!FTgrid.Row = 8 + 5 * ii
    If Multigrid!FTgrid.Text = "NA" Then
        cells(ii) = -9999
    Else
        cells(ii) = Val(Multigrid!FTgrid.Text) 'put the
'mean into an 'array
    End If
Next ii
Multigrid!FTgrid.Row = Multigrid!FTgrid.Row + 2
'Now we report the maximum of the list of 9 means
'(each mean is from the ButrNum [usually 11] sets of line
'segments analyzed for a given click point)
Multigrid!FTgrid.Col = 14
Multigrid!FTgrid.Text = Format$(maxarray(cells(), 8), "0.000")
Multigrid!FTgrid.Col = 15
Multigrid!FTgrid.Text = Format$(bsum / Ncount, "0.000")
Multigrid!FTgrid.Col = 16
Multigrid!FTgrid.Text = X
Multigrid!FTgrid.Col = 17
Multigrid!FTgrid.Text = Y
Multigrid!FTgrid.Col = 14
Multigrid!FTgrid.Row = Multigrid!FTgrid.Row + 1
Multigrid!FTgrid.Text = "Max. of means in this column"
Multigrid!FTgrid.Col = 15
Multigrid!FTgrid.Text = "Mean of maxima"
Multigrid!FTgrid.Col = 16
Multigrid!FTgrid.Text = "X"
Multigrid!FTgrid.Col = 17
Multigrid!FTgrid.Text = "Y"
```

Results

Table 2 below lists the different embossing runs used to compare single nip embossing to the double nip embossing method of this invention using a high bulk, uncreped through-air-dried tissue. Specifically, 13 soft uncreped throughdried bath tissue sheets were embossed and measured for Mean Embossing Clarity as described above. The tissues were manufactured in a layered configuration using an outer layer furnish of eucalyptus fibers and a chemical debonder and an inner layer furnish of northern softwood kraft fibers. All samples were embossed between one or two resilient backing rolls and a steel embossing roll engraved with a butterfly embossing pattern as disclosed in U.S. Des. Pat. No. 305,182 issued Dec. 26, 1989 to Peddada et al. entitled "Embossed Tissue or Similar Article", herein incorporated by reference. The engraving depth was 0.042 inch. The column headed "Mean Embossing Clarity" is the average of multiple CADEYES embossing clarity values for various embossments within a given sample. The number of separate butterfly regions examined for each sample type is given in the column labeled "Butterflies Measured". To the right of the Mean Embossing Clarity column is a column labeled "95%", which gives the half-width of the 95% confidence interval for the respective mean values to the left. The half-width of the confidence interval is estimated as $1.96s/\sqrt{n}$, where s is the sample variance of the n median or mean values obtained from analysis of n different butterfly embossments.

Samples 1 through 8 were embossed with standard single-nip techniques. Samples 9 through 13 were embossed with the double-nip method of this invention to enhance the Mean Embossing Clarity of the bulky, textured sheet. Sample 14 was unembossed. As Table 2 shows, the double-nip method of this invention enhances the relative depth of the embossed regions. For example, Sample 13, embossed with a double nip, has over twice the Mean Embossing Clarity as the sample with the best single-nip embossing clarity, Sample 1. Samples 1 and 13 are both single-ply sheets, which emboss better than two-ply sheets.

TABLE 2

Embossing Results

| Sample | Plies | Roll Hardness (Shore A) | | Butterflies Measured | Mean Embossing Clarity | 95% |
| --- | --- | --- | --- | --- | --- | --- |
| | | 1st Nip | 2nd Nip | | | |
| 1 | 1 | 40 | — | 14 | 0.071 | 0.011 |
| 2 | 1 | 40 | — | 6 | 0.054 | 0.012 |
| 3 | 2 | 40 | — | 7 | 0.055 | 0.013 |
| 4 | 2 | 40 | — | 7 | 0.047 | 0.013 |
| 5 | 1 | 40 | — | 8 | 0.061 | 0.008 |
| 6 | 1 | 40 | — | 1 | 0.030 | — |
| 7 | 2 | 40 | — | 6 | 0.065 | 0.008 |
| 8 | 2 | 40 | — | 3 | 0.047 | 0.006 |
| 9 | 1 | 40 | 90 | 10 | 0.136 | 0.013 |
| 10 | 1 | 40 | 90 | 10 | 0.085 | 0.008 |
| 11 | 2 | 40 | 90 | 12 | 0.093 | 0.009 |
| 12 | 2 | 40 | 90 | 12 | 0.075 | 0.009 |
| 13 | 1 | 75 | 90 | 11 | 0.155 | 0.005 |
| 14 | 1 | — | — | 4 | 0.011 | 0.005 |

Figure 10:
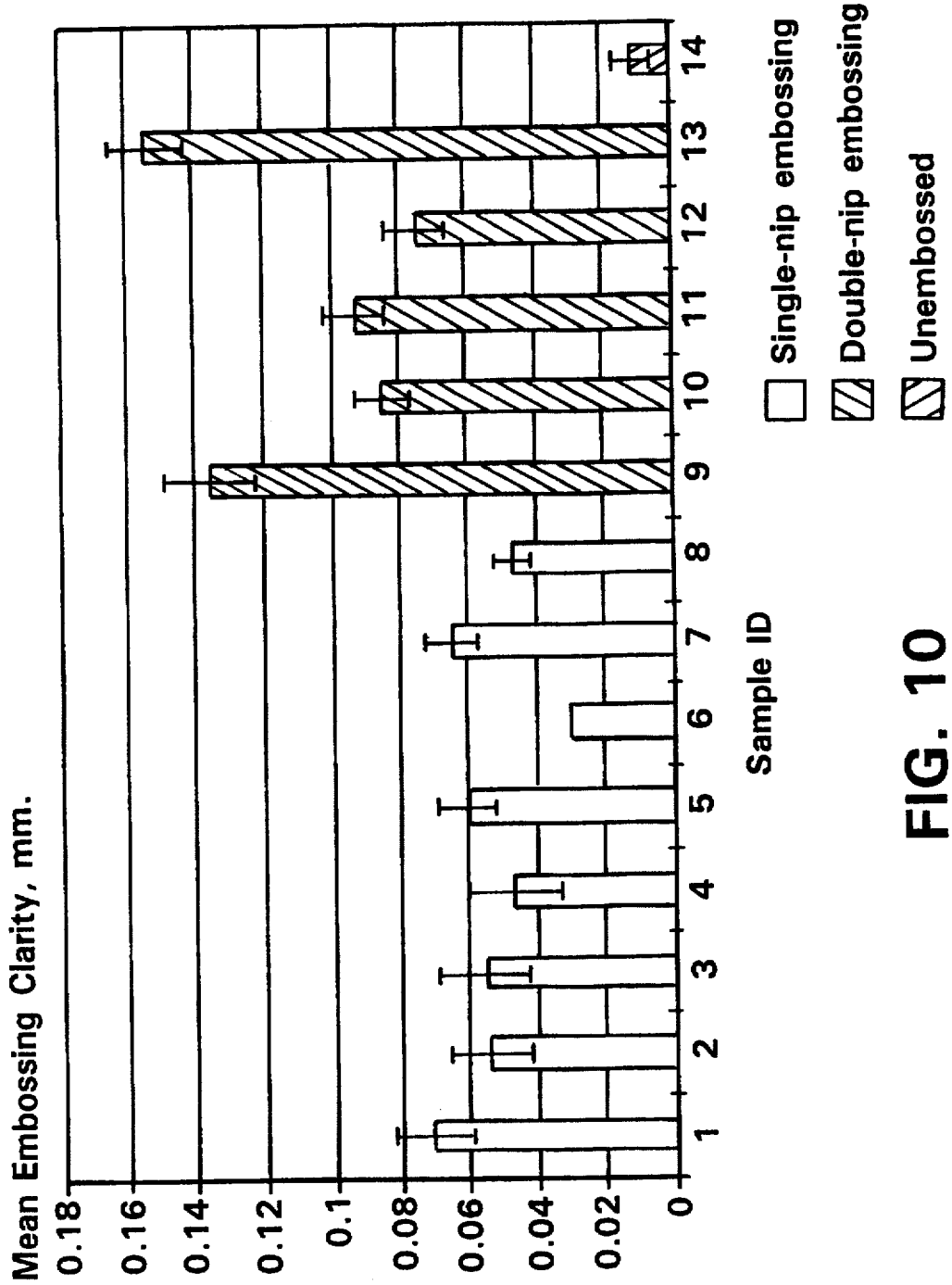
FIG. 10 is a plot of the data from Table 2, illustrating the improvement in Mean Embossing Clarity as a result of the double-nip embossing method of this invention.
Figure 11:
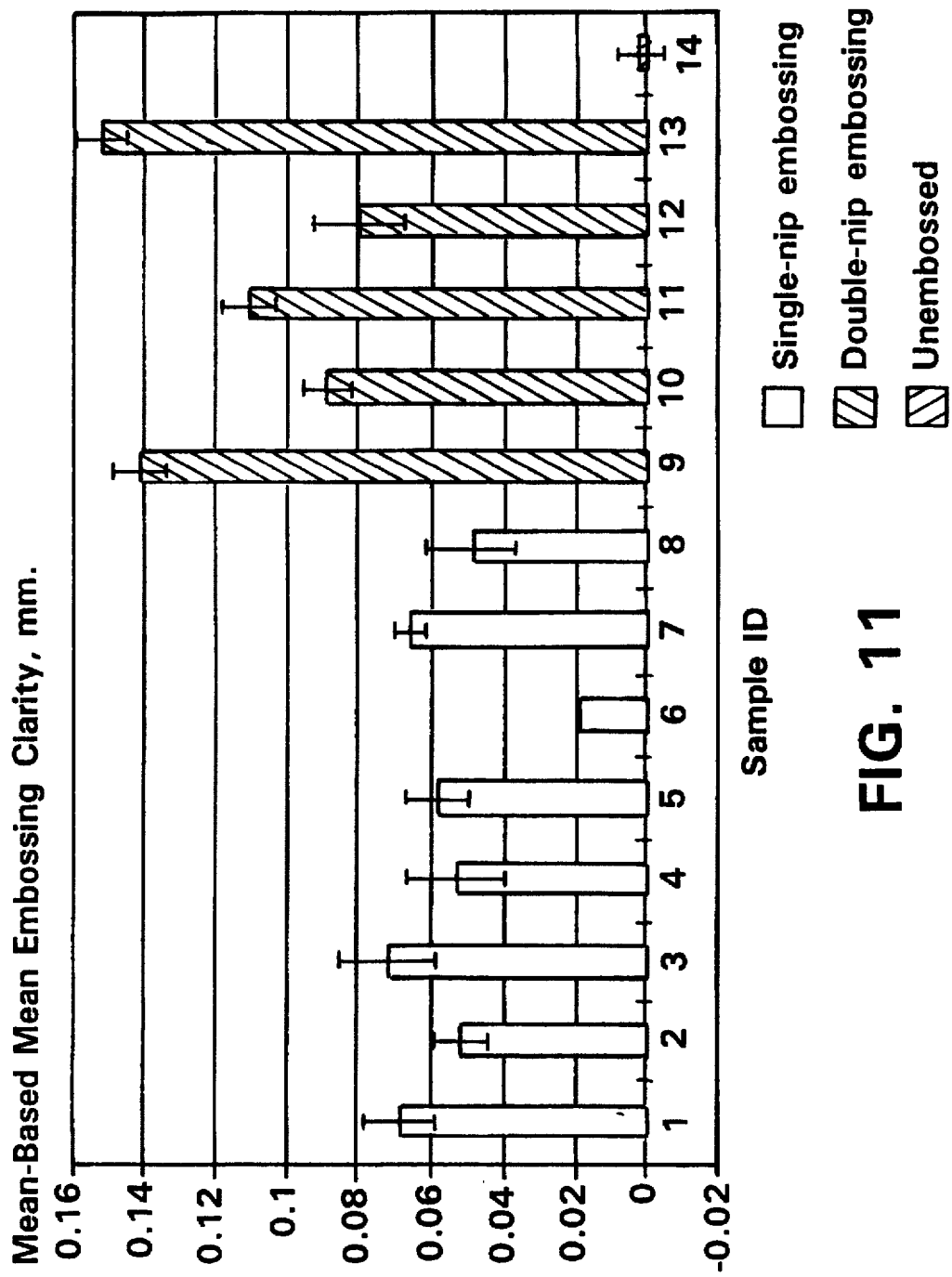
FIG. 11 is a plot similar to that of FIG. 10, but instead illustrating the improvement in a related measure designated as the "Mean-Based Mean Embossing Clarity" (hereinafter described and defined). In comparison, the Mean Embossing Clarity is a "median-based" measure as will be further described and defined below.

The results are also graphically depicted in FIG. 10. For comparison to FIG. 10, FIG. 11 illustrates the results using the Mean-Based Embossing Clarity value ("MaxMin" on FIG. 6B, for example) in the analysis of each embossment. The Mean-Based Embossing Clarity, previously described in conjunction with FIG. 6 above, is the maximum of the 9 placement-specific means (means of the 11 MnDiff values for each ensemble placement in the 3×3 scan) rather than medians. The use of means instead of medians to characterize placement-specific embossing depth gives similar results to the preferred strategy of using medians.

It will be appreciated that the foregoing examples, given for purposes of illustration, are not to be construed as limiting the scope of this invention, which is defined by the following claims and all equivalents thereto.

We claim:

1. A method of embossing a cellulosic web comprising:

(a) embossing the web in a first embossing nip formed between a rotating rigid embossing roll having a pattern of protruding embossing elements and a first rotating resilient backing roll to produce an embossed web having a pattern of embossments corresponding to the embossing elements pattern; and (b) thereafter embossing the web in a second embossing nip formed between a second rotating resilient backing roll and a second rigid embossing roll that is either the rotating rigid embossing roll or another rotating rigid embossing roll having a pattern of protruding embossing elements which is in registration with the pattern of embossments in the embossed web such that the embossing elements of the second rigid embossing roll fall within the embossments of the embossed web, wherein the Shore A hardness of the second resilient backing roll is greater than the Shore A hardness of the first resilient backing roll, thereby setting the pattern of embossments in the web and forming a twice-embossed web having improved pattern definition.

2. The method of claim 1 wherein the Shore A hardness of the second resilient backing roll is at least about 5 Shore A hardness points greater than the Shore A hardness of the first resilient backing roll.

3. The method of claim 1 wherein the Shore A hardness of the second resilient backing roll is from about 5 to about 70 Shore A hardness points greater than the Shore A hardness of the first resilient backing roll.

4. The method of claim 1 wherein the Shore A hardness of the second resilient backing roll is from about 10 to about 55 Shore A hardness points greater than the Shore A hardness of the first resilient backing roll.

5. The method of claim 1 wherein the Shore A hardness of the second resilient backing roll is from about 25 to about 40 Shore A hardness points greater than the Shore A hardness of the first resilient backing roll.

6. The method of claim 1 wherein the Shore A hardness of the first resilient backing roll is about 40 Durometer and the Shore A hardness of the second resilient backing roll is about 90 Durometer.

7. The method of claim 1 wherein the Shore A hardness of the first resilient backing roll is about 75 Durometer and the Shore A hardness of the second resilient backing roll is about 90 Durometer.

8. The method of claim 1 wherein the Shore A hardness of the first resilient backing roll is from about 30 to about 95.

9. The method of claim 1 wherein the Shore A hardness of the second resilient backing roll is from about 70 to about 100.

10. The method of claim 1 wherein the cellulosic web is an uncreped throughdried tissue web.

11. The method of claim 1 wherein the rigid embossing roll of step (a) is the rigid embossing roll of step (b).

12. The method of claim 1 wherein the rigid embossing roll of step (a) is not the same roll as the rigid embossing roll of step (b).

13. A method of embossing a soft, uncreped throughdried tissue web comprising:

(a) embossing the web in a first embossing nip formed between a first rotating resilient backing roll and a rotating rigid embossing roll having a pattern of protruding embossing elements to produce an embossed web having a pattern of embossments corresponding to the embossing elements pattern; and (b) embossing the embossed web, while supported on the surface of the rigid embossing roll, in a second embossing nip formed between the rigid embossing roll and a second rotating resilient backing roll, wherein the Shore A hardness of the second resilient backing roll is greater than the Shore A hardness of the first resilient backing roll, thereby setting the pattern of embossments in the web and forming a twice-embossed web having improved pattern definition.

14. The method of claim 13 wherein the Shore A hardness of the second resilient backing roll is at least about 5 Shore A hardness points greater than the Shore A hardness of the first resilient backing roll.

15. The method of claim 13 wherein the Shore A hardness of the second resilient backing roll is from about 5 to about 70 Shore A hardness points greater than the Shore A hardness of the first resilient backing roll.

16. The method of claim 13 wherein the Shore A hardness of the second resilient backing roll is from about 10 to about 55 Shore A hardness points greater than the Shore A hardness of the first resilient backing roll.

17. The method of claim 13 wherein the Shore A hardness of the second resilient backing roll is from about 25 to about 40 Shore A hardness points greater than the Shore A hardness of the first resilient backing roll.

18. The method of claim 13 wherein the Shore A hardness of the first resilient backing roll is about 40 Durometer and the Shore A hardness of the second resilient backing roll is about 90 Durometer.

19. The method of claim 13 wherein the Shore A hardness of the first resilient backing roll is about 75 Durometer and the Shore A hardness of the second resilient backing roll is about 90 Durometer.

20. The method of claim 13 wherein the Shore A hardness of the first resilient backing roll is from about 30 to about 95.

21. The method of claim 13 wherein the Shore A hardness of the second resilient backing roll is from about 70 to about 100.

* * * * *